US011511029B2

(12) United States Patent
Pouchoulin

(10) Patent No.: US 11,511,029 B2
(45) Date of Patent: Nov. 29, 2022

(54) APPARATUS FOR EXTRACORPOREAL TREATMENT OF BLOOD AND METHOD OF PRIMING AN EXTRACORPOREAL BLOOD CIRCUIT

(71) Applicant: GAMBRO LUNDIA AB, Lund (SE)

(72) Inventor: Dominique Pouchoulin, Tramoyes (FR)

(73) Assignee: Gambro Lundia AB, Lund (SE)

( * ) Notice: Subject to any disclaimer, the term of this patent is extended or adjusted under 35 U.S.C. 154(b) by 422 days.

(21) Appl. No.: 16/631,726

(22) PCT Filed: Jul. 4, 2018

(86) PCT No.: PCT/EP2018/068063
§ 371 (c)(1),
(2) Date: Jan. 16, 2020

(87) PCT Pub. No.: WO2019/015961
PCT Pub. Date: Jan. 24, 2019

(65) Prior Publication Data

US 2020/0179588 A1 Jun. 11, 2020

(30) Foreign Application Priority Data

Jul. 19, 2017 (EP) .................................... 17182162

(51) Int. Cl.
*A61M 1/36* (2006.01)
*A61M 39/28* (2006.01)

(52) U.S. Cl.
CPC .......... *A61M 1/369* (2013.01); *A61M 1/3626* (2013.01); *A61M 1/3627* (2013.01);
(Continued)

(58) Field of Classification Search
CPC .. A61M 1/369; A61M 1/3626; A61M 1/3627; A61M 1/3643; A61M 39/28;
(Continued)

(56) References Cited

U.S. PATENT DOCUMENTS 4,653,577 A 3/1987 Noda
6,336,910 B1 1/2002 Ohta et al.
(Continued)

FOREIGN PATENT DOCUMENTS

CN 104379186 A1 2/2015
CN 106687158 A 5/2017
(Continued)

OTHER PUBLICATIONS

First Office Action dated Feb. 9, 2022, corresponding Chinese Application No. 201880048090.8.
(Continued)

*Primary Examiner* — Susan S Su
*Assistant Examiner* — Eric Rassavong
(74) *Attorney, Agent, or Firm* — K&L Gates LLP

(57) ABSTRACT

An extracorporeal blood treatment apparatus comprises: a blood treatment device (2); an extracorporeal blood circuit comprising a blood withdrawal line (6) and a blood return line (7) coupled to the extracorporeal blood treatment device (2), wherein the blood return line (7) presents a heating zone (14) coupled or configured to be coupled to a blood warmer (15); a blood pump (6) configured to be coupled to a pump section of the blood withdrawal line (6); at least a post-infusion line (13, 13') connected to the blood return line (7) upstream of the heating zone (14); an air trapping device (9) placed on the blood return line (7) upstream of the heating zone (14).

12 Claims, 5 Drawing Sheets

(52) U.S. Cl.
CPC .......... *A61M 1/3643* (2013.01); *A61M 39/28* (2013.01); *A61M 2205/3344* (2013.01); *A61M 2205/36* (2013.01)

(58) Field of Classification Search
CPC ...... A61M 2205/3344; A61M 2205/36; A61M 1/3434; A61M 1/3437; A61M 1/153; A61M 1/1629; A61M 1/1698
See application file for complete search history.

(56) References Cited

U.S. PATENT DOCUMENTS

| | | | | |
|---|---|---|---|---|
| 6,626,857 | B1 * | 9/2003 | Ohta | A61M 1/3458 604/4.01 |
| 7,236,694 | B1 | 6/2007 | Chammas | |
| 7,588,723 | B2 | 9/2009 | Gershowitz | |
| 10,695,481 | B2 * | 6/2020 | Kelly | A61M 1/1696 |
| 10,857,277 | B2 * | 12/2020 | Kelly | A61M 1/1696 |
| 2003/0032914 | A1 | 2/2003 | Inoue et al. | |
| 2004/0219060 | A1 | 11/2004 | Maianti et al. | |
| 2005/0020958 | A1 | 1/2005 | Paolini et al. | |
| 2011/0105983 | A1 * | 5/2011 | Kelly | A61M 1/288 604/6.11 |
| 2012/0265117 | A1 * | 10/2012 | Fava | A61M 1/3629 604/6.09 |
| 2014/0217020 | A1 * | 8/2014 | Meyer | A61M 1/1696 96/182 |
| 2014/0326646 | A1 * | 11/2014 | Strohhoefer | A61M 1/1609 210/85 |
| 2016/0310656 | A1 * | 10/2016 | Vinci | A61M 1/342 |
| 2016/0361485 | A1 * | 12/2016 | Tényi | A61M 1/3424 |

FOREIGN PATENT DOCUMENTS

| | | | |
|---|---|---|---|
| EP | 0834329 | A1 | 4/1998 |
| EP | 1061971 | A1 | 12/2000 |
| EP | 2133107 | A1 | 12/2009 |
| EP | 2995329 | A1 | 3/2016 |
| WO | WO 0064510 | A1 | 11/2000 |
| WO | WO 03055543 | A1 | 7/2003 |
| WO | WO 2004105589 | A2 | 12/2004 |
| WO | WO 2006047147 | A1 | 5/2006 |
| WO | WO 2006111281 | A1 | 10/2006 |
| WO | WO 2011019655 | A2 | 2/2011 |

OTHER PUBLICATIONS

International Search Report; International Application No. PCT/EP2018/068063; dated Aug. 21, 2018; 4 Pages.

Written Opinion of the International Searching Authority; International Application No. PCT/EP2018/068063; dated Aug. 21, 2018; 7 Pages.

European Search Report; European Application No. 17182162.2; dated Jan. 15, 2018; 13 Pages.

* cited by examiner

17'
9
24
14
15
7
22
13'
23
16
21
17
13
20

17'
9
24
14
15
7
22
13'
23
16
21
17
13
20

17'
9
24
14
15
7
22
13'
16
21
17
13
25
20

APPARATUS FOR EXTRACORPOREAL TREATMENT OF BLOOD AND METHOD OF PRIMING AN EXTRACORPOREAL BLOOD CIRCUIT

PRIORITY CLAIM

The present application is a National Phase of International Application No. PCT/EP2018/068063, filed Jul. 4, 2018, which claims priority to EP Application No. 17182162.2, filed Jul. 19, 2017, the entire contents of each of which are incorporated herein by reference and relied upon.

FIELD OF THE INVENTION

The present invention relates to an apparatus for extracorporeal treatment of blood. The extracorporeal treatment apparatus according to the invention is combined with, or comprises, a blood-warming device. The invention also concerns a method of priming an extracorporeal blood circuit, before starting patient treatment, wherein the blood-warming device may be part of the extracorporeal blood treatment apparatus or may be a separate device which is in communication with the extracorporeal blood treatment apparatus.

Extracorporeal blood treatment involves removing blood from a patient, treating the blood externally to the patient, and returning the treated blood to the patient. Extracorporeal blood treatment is typically used to extract undesirable matter or molecules from the patient's blood and/or add desirable matter or molecules to the blood. Extracorporeal blood treatment is used with patients unable to effectively remove matter from their blood, such as when a patient has suffered temporary or permanent kidney failure. These patients and other patients may undergo extracorporeal blood treatment to add or remove matter to their blood, to maintain an acid/base balance or to remove excess body fluids, for example.

Extracorporeal blood treatment is typically accomplished by removing the blood from the patient in e.g. a continuous flow, introducing the blood into a primary chamber, also referred to as blood chamber, of a treatment unit (such as a dialyzer or an hemofilter) where the blood is allowed to flow past a semipermeable membrane. The semipermeable membrane selectively allows matter in the blood to cross the membrane from the primary chamber into a secondary chamber and also selectively allows matter in the secondary chamber to cross the membrane into the blood in the primary chamber, depending on the type of treatment.

A number of different types of extracorporeal blood treatments may be performed. In an ultrafiltration (UF) treatment, undesirable fluid is removed from the blood by convection across the membrane into the secondary chamber. In a hemofiltration (HF) treatment, the blood flows past the semipermeable membrane as in UF (where waste and undesirable fluid are removed) and desirable matter is added to the blood, typically by dispensing a fluid into the blood either before and/or after it passes through the treatment unit and before it is returned to the patient. In a hemodialysis (HD) treatment, a secondary fluid containing desirable matter is introduced into the secondary chamber of the treatment unit. Undesirable matter from the blood crosses the semipermeable membrane into the secondary fluid by diffusion and desirable matter from the secondary fluid crosses the membrane into the blood. In a hemodiafiltration (HDF) treatment, blood and secondary fluid exchange matter as in HD, and, in addition, matter is added to the blood, typically by dispensing a fluid into the treated blood (infusion) either before and/or after it passes through the treatment unit and before its return to the patient as in HF.

During extracorporeal blood treatment therapies, the patient may loose significant amount of heat due to infusion fluids having lower temperature than blood, due to fluid exchange across the membrane of the treatment unit, and due to heat lost to the atmosphere. As extracorporeal blood treatments may last from several hours up to several days, the patient is put at risk of hypothermia in case no preventive measures are taken. This risk is, for example, present both in the case of relatively short treatments with high volume exchange, like chronic HD or HDF, and in the case of low volume but continuous therapies like continuous renal replacement therapy (CRRT) (used in e.g. acute HD). Furthermore, the risk of hypothermia is even more problematic in case of treatments applied to low body weight patients, such as children. Blood cooling due to fluid exchange (treatment and/or infusion fluids) is usually more important than heat losses to atmosphere in the complete extracorporeal blood circuit. In order to prevent hypothermia during extracorporeal blood treatment several solutions have been developed in the past.

BACKGROUND

In accordance with a known solution, and in order to solve the above problems, blood warmers acting on the bloodline and capable of directly warming blood have been used. Blood warming brings the benefit of operating the filter device (in hemodialysis—HD—, hemodiafiltration—HDF—or hemofiltration in pre-dilution—HFpre—therapies) at a cooler temperature with respect to warming the therapy fluids, since using room temperature fluids. Cooler blood temperature in the filter device is expected to decrease intensity of blood-materials interactions, thus improving biocompatibility and reducing clotting risks.

Document WO 00/41746 discloses an integrated CRRT method and apparatus which incorporates steps and devices for compensating for heat loss from blood in an extracorporeal circuit. A blood warmer is designed to engage and hold a disposable blood tube segment to transfer heat at a closely controlled temperature to blood flowing in the disposable blood tube segment. The blood tube segment for engagement with the blood warmer is located in downstream of a dialyzer and upstream of a venous pressure monitor, an air bubble detector and a venous line clamp. The disposable blood tube segment may be selectively connected when heat loss compensation is required and left disconnected when heat loss compensation is not required.

Document U.S. Pat. No. 6,336,910 B1 discloses an extracorporeal circulation apparatus used when conducting a cooling method employed in various medical treatments in humans. A diluent from a diluent container is cooled in a heat exchanger and injected into the body. Blood is withdrawn from the catheter, it passes through a blood concentration device, it is heated to a temperature near 37° C. in the heat exchanger and then it is injected back into the body via a catheter. The concentration of the blood means the increase in or the recovery of the hematocrit value of the diluted blood drawn out from a body may be performed by means of a filtration or dialysis treatment. Such a treatment may be performed by using an ordinary hemofilter which is used in an artificial kidney apparatus. A drip chamber for removing bubbles may be provided between the concentration element and the heat exchanger.

A disadvantage of the cited prior art documents may concern the safety of the extracorporeal blood treatment apparatuses provided with blood-warming devices for heat compensation. Indeed, air bubbles contained in blood flowing through the blood-warming device (air trapping in the blood-warming device) may lead to development of 'hot spots' and heating problems in the blood-warming device and/or may lead to early clotting of the blood circuit. Such events may lead to blood loss and put patient safety at risk if recurring over time.

In addition, this fact may generate significant constraints in the blood-warming device design and may cause an increase of their design and production costs, since said blood-warming devices shall be designed not to trap any bubbles.

In particular, these problems are crucial for those apparatuses for extracorporeal treatment of blood provided with high infusion rates and large number of infusion lines, since blood is cooled a lot and the blood-warming device shall provide a large amount of heat to the blood to restore the correct temperature.

SUMMARY OF THE INVENTION

In view of the above, it is an object of the present invention to improve the safety of extracorporeal blood treatment apparatuses coupled to a blood-warming device (wherein the blood-warming device may be part of the extracorporeal blood treatment apparatus or may be a separate device, which is in communication with the extracorporeal blood treatment apparatus).

It is a further object of the present invention to provide an apparatus for extracorporeal treatment of blood which allows to reduce or prevent air trapping in the blood-warming device. It is a further object of the present invention to provide an apparatus for extracorporeal treatment of blood which allows to protect the blood-warming device from the repeated presence of air bubbles at its flow inlet.

At least one of the above objects is substantially achieved by providing an air trapping device at the inlet of the blood warming device placed on the blood return line of the apparatus for extracorporeal treatment of blood.

Aspects of the invention are disclosed in the following.

In accordance with a 1$^{st}$ independent aspect, an extracorporeal blood treatment apparatus comprises:

a blood treatment device;

an extracorporeal blood circuit comprising a blood withdrawal line and a blood return line coupled to the blood treatment device, wherein the blood return line presents a heating zone coupled or configured to be coupled to a blood warmer;

a blood pump configured to be coupled to a pump section of the extracorporeal blood circuit, e.g. of the blood withdrawal line or of the blood return line;

at least a post-infusion line connected to the blood return line upstream of the heating zone;

an air trapping device placed on the blood return line upstream of the heating zone.

This configuration allows to prevent air intake at the blood warmer inlet. Since air intake is prevented, more design options may be considered for the warmer: freedom on warmer orientation (e.g. vertical bag) and freedom in warmer concept. Optionally, the blood treatment device has a first compartment or blood chamber and a second compartment or fluid chamber separated from one another by a semipermeable membrane; the blood withdrawal line is connected to an inlet port of the blood chamber; the blood return line is connected to an outlet port of the blood chamber.

Optionally, the apparatus comprises a fluid evacuation line connected with an outlet port of the fluid chamber.

Optionally, the apparatus comprises a dialysis line connected to an inlet port of the fluid chamber.

In a 2$^{nd}$ aspect according to the previous aspects, the post-infusion line is connected to the air trapping device.

In another aspect, the post-infusion line may be connected to the blood return line upstream of the air trapping device.

In a 3$^{rd}$ aspect according to the previous aspects, the extracorporeal blood treatment apparatus comprises a secondary post-infusion line in fluid communication with the blood return line upstream of the heating zone and connected to said blood return line downstream of the heating zone, to bypass the blood warmer. The post-infusion circuit is split in two streams: a main stream connected to the air trapping device and a secondary stream connecting the blood circuit downstream of the blood warmer. The main stream flows through a line segment of the post-infusion line comprised between a branching off point and the air trapping device. The secondary stream flows through the secondary post-infusion line.

In a 4$^{th}$ aspect according to the previous aspect, upstream of the heating zone, the secondary post-infusion line is connected to the post-infusion line.

In a 5$^{th}$ aspect according to aspects 3 or 4, the secondary post-infusion line is connected to the post-infusion line upstream of the air trapping device.

In another aspect, the secondary post-infusion line is connected to the air trapping device.

In a 6$^{th}$ aspect according to any of aspects 3 to 5, the apparatus comprises control devices operatively active on the post-infusion line and on the secondary post-infusion line, for controlling a flow through said post-infusion line and through said secondary post-infusion line, optionally through the line segment of said post-infusion line and through said secondary post-infusion line.

In a 7$^{th}$ aspect according to the previous aspect, the control devices comprises a by-pass pump placed on the secondary post-infusion line, optionally said by-pass pump is a peristaltic pump, optionally said by-pass pump is a finger pump, optionally said pump is a diaphragm pump. Use of a peristaltic pump on the secondary post-infusion line prevents blood from by-passing the blood warmer in case the post-infusion flow is stopped during treatment. The peristaltic pump allows for continuous flow in the secondary post-infusion line. The flow rate in this line may be in the range of 50 ml/h to 6000 ml/h, optionally of 50 ml/h to 4000 ml/h, optionally of 50 ml/h to 2000 ml/h. In case the set post-infusion flow rate is in the same order of magnitude, the pump may operate in a periodic mode. Continuous or periodic flow in the secondary post-infusion line prevents blood clotting at its connection with the blood circuit, as well as blood back-flow in the case a pressure pod is implemented in this circuit section.

In a 8$^{th}$ aspect according to aspect 6, the control devices comprises a pinch valve placed between the post-infusion line and the secondary post-infusion line at a branching off point of the secondary post-infusion line.

In a 9$^{th}$ aspect according to aspect 6, the control devices comprises a flow resistor placed on the secondary post-infusion line.

In a 10$^{th}$ aspect according to aspect 6, the control devices comprises a secondary post-infusion clamp placed on the secondary post-infusion line.

In a 11$^{th}$ aspect according to the previous aspect 9 or 10, the control devices comprises a post-infusion clamp placed on the post-infusion line downstream of the branching off point of the secondary post-infusion line. The post-infusion clamp is placed on the line segment.

In a 12$^{th}$ aspect according to the previous aspect 9 or 10, the control devices comprises a non-return valve placed on the post-infusion line downstream of the branching off point of the secondary post-infusion line. The non-return valve is placed on the line segment.

In a 13$^{th}$ aspect according to the previous aspects, a return pressure sensor is placed on the blood return line downstream of the heating zone.

In a 14$^{th}$ aspect according to the previous aspects form 3 to 12, a return pressure sensor is placed on the secondary post-infusion line. The presence of the return pressure sensor on the secondary post-infusion line, instead of in the blood return line, allows to monitor the return pressure as well as the blood warmer pressure drop and prevents additional clotting risks.

In a 15$^{th}$ aspect according to the previous aspects, an auxiliary air trapping device is placed downstream of the heating zone.

In a 16$^{th}$ aspect according to the previous aspect, the auxiliary air trapping device is identical to the air trapping device.

In a 17th aspect according to previous aspect 15 or 16, a return pressure sensor is operatively active in the auxiliary air trapping device.

In a 18$^{th}$ aspect according to previous three aspects when aspect 14 refers to anyone of aspects from 3 to 12, the secondary post-infusion line is connected to the blood return line downstream of the heating zone at the auxiliary air trapping device. Adding the auxiliary air trapping device downstream the blood warmer is a better solution from the robustness and usability point of view, since any remaining air bubble at the end of the secondary post-infusion line is evacuated in the auxiliary air trapping device.

In a 19$^{th}$ aspect according to previous aspect 15, the auxiliary air trapping device is a filled air trap.

In a 20$^{th}$ aspect according to the previous aspect, the extracorporeal blood treatment apparatus comprises an auxiliary blood line connecting a top of the filled air trap to the air trapping device.

In a 21$^{st}$ aspect according to the previous aspect, an auxiliary blood pump is placed on the auxiliary blood line and it is configured to pump blood from the filled air trap back to air trapping device. The auxiliary blood pump ensures a continuous flow from the blood filled air trap to the air trapping device, in order to both remove air bubbles as soon as they are captured in the filled air trap, and to prevent clotting in the auxiliary blood line between the two chambers. This circuit design allows operating the blood warmer 15 in safe conditions with respect to warming accuracy and clotting risk by preventing too low flow rate and most flow stops inside the blood warmer 15, thanks to the recirculation loop. This recirculation capability in the blood warmer 15 allows also for designing, if needed, degassing manoeuvres during the priming sequence, with the possibility to create and alternate positive and negative pressure in the warmer circuit section. In a 22$^{nd}$ aspect according to the previous aspects, a warmer clamp is placed on the blood return line between the air trapping device and the heating zone. The secondary post-infusion line and the warmer clamp make possible to by-pass the blood warmer during the early priming steps where an air-fluid mixture flows out from the blood treatment device, with a switch back to normal flow in the blood warmer once most of air bubbles have been removed and the air chamber of the air trapping device has become fully effective in removing the remaining air bubbles.

Circuit variants with two chambers (air trapping device and auxiliary air trapping device) may not require any warmer clamp in the blood circuit section including the blood warmer, provided that limited amounts of air will remain in the device at the end of the priming sequence.

In a 23$^{rd}$ aspect according to the previous aspects, an air bubble detector is placed downstream of the heating zone. The downstream position of the air bubble detector has the benefit to prevent any trouble in case of priming defects and subsequent release of air during therapy, like risk of patient air embolism or risk of air infusion to patient.

In a 24$^{th}$ aspect according to the previous aspects, a pressure monitor is operatively active in the air trapping device.

In a 25$^{th}$ aspect according to the previous aspects, the apparatus comprises a blood warmer operatively active on the heating zone, in particular the blood return line being engaged with the blood warmer 20 so that the blood warmer 20 is arranged to transfer heat to blood flowing in the blood return line at the heating zone, for example the blood return line including a warmer bag at the heating zone. The warmer bag may comprise two films defining a blood path therebetween from an inlet to an outlet for the blood.

In accordance with 26$^{th}$ independent aspect, a method for priming an extracorporeal blood circuit of an extracorporeal blood treatment apparatus, optionally through the apparatus according to anyone of the previous aspects, before starting patient treatment, comprises:

filling the extracorporeal blood circuit of the extracorporeal blood treatment apparatus with a priming fluid and making the priming fluid flowing at least through a blood treatment device and through at least a blood return line towards a heating zone of said blood return line;

wherein, during an initial time interval, the priming fluid is diverted into a secondary post-infusion line, in fluid communication with the blood return line upstream of the heating zone and connected to the blood return line downstream of the heating zone, to bypass a blood warmer operatively active on said heating zone;

wherein, after said initial time interval, the diversion is interrupted so that the priming fluid flows through an air trapping device placed on the blood return line upstream of the heating zone and then through said heating zone towards a terminal end of the blood return line.

In a 27$^{th}$ aspect according to previous aspect 26, during the initial time interval, the priming fluid flows through a post-infusion line connected to the blood return line upstream of the heating zone.

In a 28$^{th}$ aspect according to previous aspect 26 or 27, after the initial time interval, the priming fluid flows through a post-infusion line connected to the blood return line upstream of the heating zone.

In 29$^{th}$ aspect according to previous aspect 26, 27 or 28, during the initial time interval, the priming fluid flows through the air trapping device.

In 30$^{th}$ aspect according to one of previous aspects from 26 to 29, during the initial time interval, the priming fluid flows from the blood return line placed upstream of the heating zone, through the air trapping device and then into the secondary post-infusion line.

In a 31$^{st}$ aspect according to one of previous aspects from 26 to 29, after the initial time interval, the priming fluid flows from a post-infusion line connected to the blood return line upstream of the heating zone, through the air trapping device and then into the blood return line downstream of the air trapping device.

In a 32$^{nd}$ aspect according to one of previous aspects from 26 to 31, after said initial time interval, the priming fluid, flowing through a post-infusion line connected to the blood return line upstream of the heating zone, is split into the air trapping device and into the secondary post-infusion line.

In a 33$^{rd}$ aspect according to one of previous aspects from 26 to 32, during the initial time interval, a warmer clamp placed on the blood return line between the air trapping device and the heating zone is closed, thus allowing the priming fluid coming from the post-infusion line and the priming fluid coming from the blood return line and flowing through the air trapping device to flow through the secondary post-infusion line.

In a 34$^{th}$ aspect according to the previous aspect, after the initial time interval, the warmer clamp is open, thus allowing the priming fluid coming from the post-infusion line to flow through the secondary post-infusion line and/or into the air trapping device and allowing the priming fluid coming from the blood treatment device to flow through the air trapping device and through the heating zone.

In a 35$^{th}$ aspect according to the previous aspects 33 or 34, during the initial time interval a pinch valve, placed between the main post-infusion line and the secondary post-infusion line at a branching off point of the secondary post-infusion line, is set in a neutral position so that the air trapping device is in fluid communication with the secondary post-infusion line.

In a 36$^{th}$ aspect according to the previous aspects 33 or 34, during the initial time interval a post-infusion clamp, placed on the post-infusion line downstream of the branching off point of the secondary post-infusion line, is open so that the air trapping device is in fluid communication with the secondary post-infusion line.

DESCRIPTION OF THE DRAWINGS

The following drawings relating to aspects of the invention are provided by way of non-limiting example.

DETAILED DESCRIPTION

Figure 1:
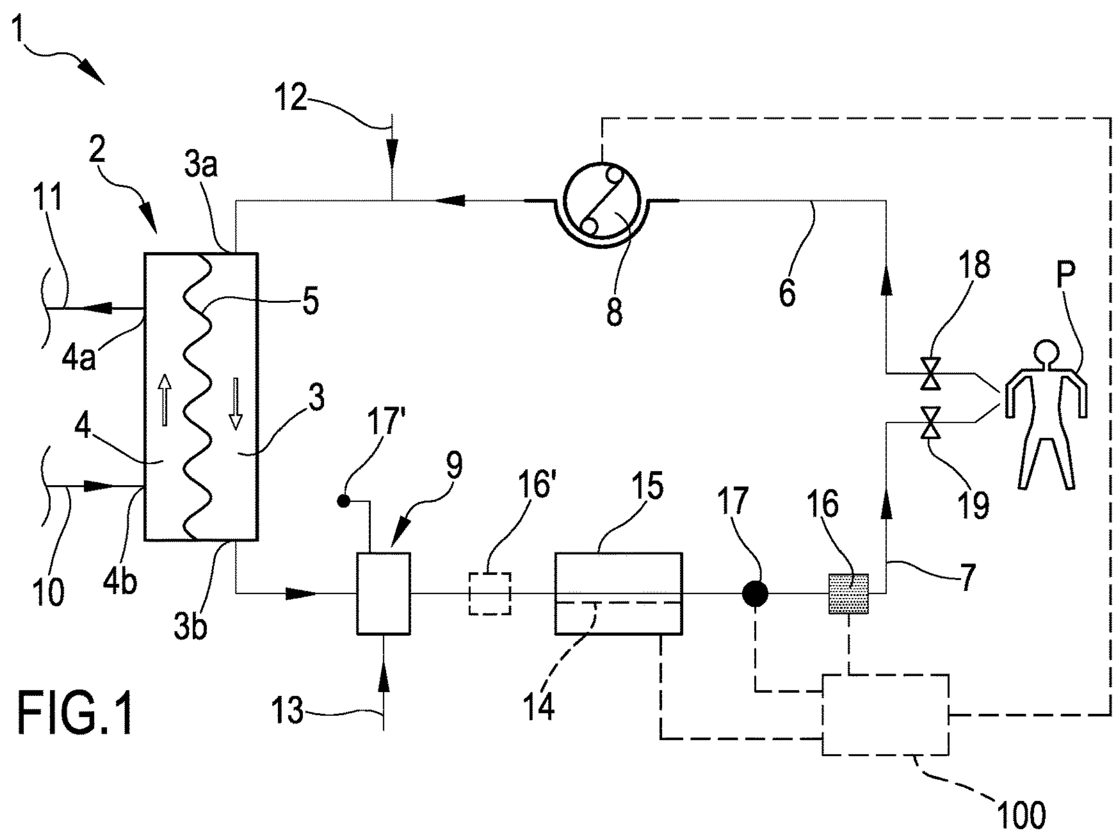
FIG. 1 shows a schematic representation of an extracorporeal blood treatment apparatus provided with an air trapping device and of a blood warmer according to the invention.

With reference to the appended drawings, FIG. 1 shows a schematic representation of an extracorporeal blood treatment apparatus 1.

The apparatus 1 comprises one blood treatment device 2, for example a hemofilter, a hemodiafilter, a plasmafilter, a dialysis filter, a membrane oxygenator, an adsorption device or other unit suitable for processing the blood taken from a patient P. The blood treatment device 2 has a first compartment or blood chamber 3 and a second compartment or fluid chamber 4 separated from one another by a semipermeable membrane 5. A blood withdrawal line 6 is connected to an inlet port 3*a* of the blood chamber 3 and is configured, in an operative condition of connection to the patient P, to remove blood from a vascular access device inserted, for example in a fistula on the patient P. A blood return line 7 connected to an outlet port 3*b* of the blood chamber 3 is configured to receive treated blood from the treatment unit 2 and to return the treated blood, e.g. to a further vascular access also connected to the fistula of the patient P. Note that various configurations for the vascular access device may be envisaged: for example, typical access devices include a needle or catheter inserted into a vascular access which may be a fistula, a graft or a central (e.g. jugular vein) or peripheral vein (femoral vein) and so on. The blood withdrawal line 6 and the blood return line 7 are part of an extracorporeal blood circuit of the apparatus 1.

The extracorporeal blood circuit 6, 7 and the treatment unit 2 are usually disposable parts which are loaded onto a frame of a blood treatment machine, not shown.

As shown in FIG. 1, the apparatus 1 comprises at least a first actuator, in the present example a blood pump 8, which is part of said machine and operates at the blood withdrawal line 6, to cause movement of the blood removed from the patient P from a first end of the withdrawal line 6 connected to the patient P to the blood chamber 3. The blood pump 8 is, for example, a peristaltic pump, as shown in FIG. 1, which acts on a respective pump section 6*a* of the withdrawal line 6. When rotated, e.g., clockwise, the blood pump 8 causes a flow of blood along the blood withdrawal line 6 towards the blood chamber 3 (see the arrows in FIG. 1 indicative of the blood flow along the blood withdrawal line 6).

It should be noted that for the purposes of the present description and the appended claims, the terms "upstream" and "downstream" may be used with reference to the relative positions taken by components belonging to or operating on the extracorporeal blood circuit. These terms are to be understood with reference to a blood flow direction from the first end of the blood withdrawal line 6 connected to the patient P towards the blood chamber 3 and then from the blood chamber 3 towards a second end of the blood return line 7 connected to the vascular access of the patient P.

The apparatus 1 further comprises an air trapping device 9 operating on the blood return line 7 (the air trapping device 9 is a venous deaeration chamber). The air trapping device 9 is placed online in the blood return line 7.

A first section of the blood return line 7 puts in fluid communication the outlet port 3*b* of the blood chamber 3 with the air trap 9 and a second section of the blood return line 7 puts in fluid communication the air trap 9 with the patient P.

The blood coming from the blood chamber 3 of the treatment device 2 enters and exits the air trap 9 before reaching the patient P.

The apparatus 1 further comprises one fluid evacuation line 11 connected with an outlet port 4*b* of the fluid chamber 4 such as to receive at least a filtered fluid through the semipermeable membrane 5. The evacuation line 11 receives the waste fluid coming from the fluid chamber 4 of the treatment device 2, for example, comprising used dialysis liquid and/or liquid ultra-filtered through the membrane 5. The evacuation line 11 leads to a receiving element, not shown, for example having a collection bag or a drainage pipe for the waste fluid. One or more dialysate pumps, not shown, may operate on the evacuation line 11.

In the example of FIG. 1, a dialysis line 10 is also present, for supplying a fresh treatment fluid to an inlet port 4*a* of the fluid chamber 4. The presence of this dialysis line 10 is not strictly necessary since, in the absence of the dialysis line, the apparatus 1 is still able to perform treatments such as ultrafiltration, hemofiltration or plasma-filtration. In case the dialysis line 10 is present, a fluid flow intercept device may be used, not shown, to selectively allow or inhibit fluid passage through the dialysis line 10, depending on whether or not a purification by diffusive effect is to be performed inside the treatment device 2.

The dialysis line 10, if present, is typically equipped with a dialysis pump, not shown, and is able to receive a fresh fluid from a module, for example a bag or on-line preparation section of dialysis fluid, and to send such a fluid to the inlet port 4*a* of the fluid chamber 4. The fluid evacuation line 11, the dialysis line 10, and the fluid chamber 4 are part of a treatment fluid circuit.

Finally, the apparatus 1 as shown comprises an infusion circuit comprising one or more infusion lines 12, 13 of a replacement fluid: for example a pre-infusion line 12 may be connected to the blood withdrawal line 6 and/or a post-infusion line 13 may be connected to the blood return line 7. Infusion pump or pumps, not shown, equips typically the infusion circuit. The pre- and/or post-infusion lines 12, 13 may be supplied by fluid coming from bags or directly by infusion fluid prepared on-line.

The post-infusion line 13 is connected to the blood return line 7 through the air trapping device 9 to supply fluid to the blood at said air trapping device 9. According to a different embodiment, not shown, the post-infusion line 13 is connected to the blood return line 7 upstream the air trapping device 9.

Downstream of the air trapping device 9, the blood return line 7 presents a heating zone 14 coupled or configured to be coupled to a blood warmer 15. It follows that the post-infusion line 13 is connected to the blood return line 7 upstream of the heating zone 14 and that the air trapping device 9 is placed on the blood return line 7 upstream of the heating zone 14.

The blood warmer 15 is associated with the apparatus 1 to form an assembly which is structured to treat blood and keep blood within predetermined desired temperature boundaries. The blood warmer 15 may be an independent device (e.g. a stand alone unit physically separated from the apparatus 1) cooperating with the apparatus 1 and—in particular—warming the heating zone 14. Alternatively, the blood warmer 15 may be a component of the apparatus 1. In this case the blood warmer 15 is not an independent stand alone unit, but rather part of the apparatus 1.

In both cases, the blood warmer 15 has a heating unit, not shown, configured for receiving and heating the heating zone of the blood return line 7. For instance, the heating zone 14 of the blood return line 7 may be in the form of a substantially flat bag insertable in a heating seat provided in the heating unit of the blood warmer. The flat bag presents an inlet and an outlet connected to the extracorporeal blood circuit. Alternatively, the heating zone 14 may include a section of the tubing or a rigid cassette inserted into the heating unit of the blood warmer 15, which heating unit for instance may comprise a heating sleeve or a heating coil wound around the heating zone 14. In practice the heating unit has heating elements (e.g. electric impedances, infrared emitters or other types of heating elements) configured to heat the corresponding heating zone 14 of the blood return line 7.

In the embodiment shown in FIG. 1, an air bubble detector 16 is placed downstream of the heating zone 14, between a terminal end with access device of the blood return line 7, connected to the patient P, and said heating zone 14.

In order to make possible troubleshooting of air bubble detector 16 alarms, the blood return line 7 may also include a puncture site, not shown, upstream the air bubble detector 16 and clamp for the air removal procedure.

A return pressure sensor 17 is placed on the blood return line 7, between the heating zone 14 and the air bubble detector 16, to monitor pressure downstream of the blood warmer 15. Pressure upstream the blood warmer 15 may be monitored in the air trapping device 9 through a pressure monitor 17' which is operatively active in said air trapping device 9, by way of example through an air filled service line required for a level adjustment in the air trapping device 9.

The apparatus shown in FIG. 1 further comprises a withdrawal clamp 18 placed close to a terminal end of the blood withdrawal line 6 and a return clamp 19 placed close to the terminal end of the blood return line 7.

The air bubble detector 16 is connected to a control unit 100 of the apparatus 1 and sends to the control unit 100 signals for the control unit 100 to cause closure of the return clamp 19 in case one or more bubbles above predetermined safety thresholds are detected.

The control unit 100, during treatment, may be configured to control the blood pump 8 based, by way of example, on a set blood flow rate. The control unit 100 of the apparatus 1 may also be configured to control the flow rate of dialysis fluid through the dialysis line 10, of evacuation fluid through the evacuation line 11, of infusion fluid/s through pre-infusion line 12 and post-infusion line 13.

The control unit 100 of the apparatus 1 may also be configured to control the blood warmer 15, during treatment, to keep blood within said desired temperature boundaries. The control unit 100 may comprise a digital processor (CPU) and memory (or memories), an analog circuit, or a combination thereof.

In use, during patient P treatment, the blood coming from the extracorporeal blood treatment device 2 and the infusion fluid flowing in the post-infusion line 13 enter the air trapping device 9 before flowing through the heating zone 14. This allows to prevent air intake at the blood warmer 15 inlet.

In addition, the air trapping device 9 may have at least a low level liquid sensor, not shown in figures, alerting the operator for adjusting the chamber level of said air trapping device 9 before air bubbles are moved to the blood warmer and to the air bubble detector 16. Alternatively, the circuit may include a second air bubble detector 16' (dashed line in FIG. 1) located immediately downstream of the air trapping device 9. The apparatus 1 of FIG. 1 is fully robust to the presence of some air bubbles in the post-infusion fluid.

Figure 2:
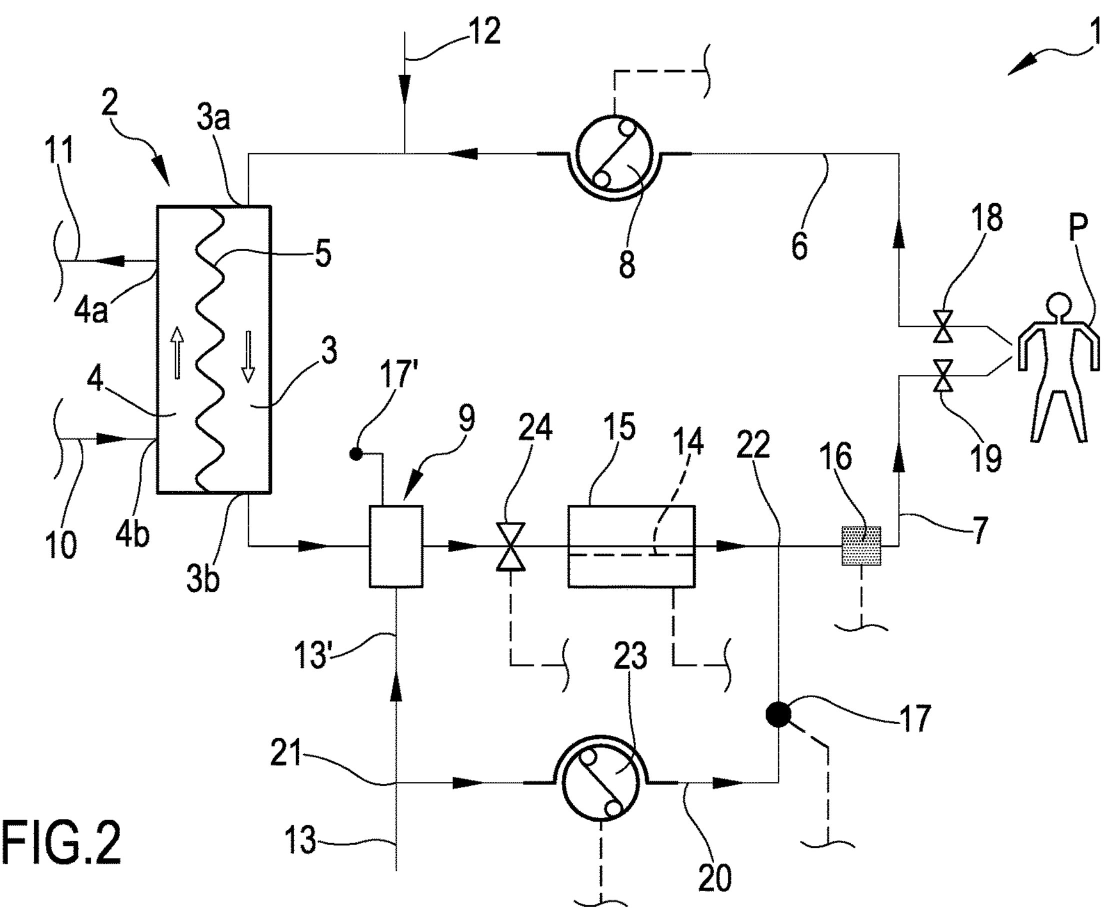
FIG. 2 shows another embodiment of the apparatus of FIG. 1.

With respect to the apparatus of FIG. 1, the apparatus 1 shown in FIG. 2 further comprises a secondary post-infusion line 20. Said secondary post-infusion line 20 is connected to the post-infusion line 13 at a branching off point 21 located upstream of the air trapping device 9. The post-infusion line 13 of the apparatus of FIG. 2 has a line segment 13' comprised between the branching off point 21 and the air trapping device 9. In another embodiment, not shown, the secondary post-infusion line 20 is connected to the air trapping device 9 (the branching off point 21 is located on the air trapping device 9). Said secondary post-infusion line 20 is connected to the blood return line 7 at a connection point 22 placed downstream of the heating zone 14 and upstream of the air bubble detector 16. In this way, the secondary post-infusion line 20 by-passes the heating zone 14 and the blood warmer 15.

A by-pass pump 23 is placed on the secondary post-infusion line 20. The return pressure sensor 17 is placed on the secondary post-infusion line 20 too (instead of on the blood return line 7 like in FIG. 1). A warmer clamp 24 is placed on the blood return line 7 between the air trapping device 9 and the heating zone 14. The by-pass pump 23 and the warmer clamp 24 are connected to the control unit 100, not shown in FIG. 2. The by-pass pump 23 is a control device operatively active on the secondary post-infusion line 20, for controlling a flow through said secondary post-infusion line 20.

In use, during patient P treatment (FIG. 2) the warmer clamp 24 is open, the return clamp 19 is open and the heating zone 14 is placed in the blood warmer 15. The blood coming from the extracorporeal blood treatment device 2 and all or part of the infusion fluid flowing in the post-infusion line 13 enter the air trapping device 9 before flowing through the heating zone 14. This allows to prevent air intake at the blood warmer 15 inlet. Through the by-pass pump 23, it is also possible to control the post-infusion flow which is split between the air trapping device and the return circuit downstream of the blood warmer 15. The post-infusion flow rate may be in the range of 50 ml/h to 6000 ml/h. The by-pass pump 23 may operate in continuous or in periodic mode. The blood warmer 15 may slightly overheat blood as to balance for the cooling effect of the secondary post-infusion, depending on the flow rates.

The presence of the secondary post-infusion line 20 during treatment may require additional means in case the post-infusion contains some air bubbles. As infusion of such air bubbles downstream the blood warmer 15 will create difficult troubleshooting situations, it may be of interest to prevent these events by: stopping temporarily flow in the secondary post-infusion line 20 when presence of air bubbles is suspected (e.g. after a bag change); adding an air detector on the post-infusion 13 upstream the post-infusion line split (an optical detection may be suitable for this purpose); having preventing means in the post-infusion 13, such as a self-venting chamber using an hydrophobic membrane, and taking advantage of the positive pressure present in the post-infusion 13 upstream the air trapping device 9.

According to a method of the invention, the apparatus detailed above and shown in FIG. 2 allows to control the flow of a priming fluid through the heating zone 14, through the infusion line 13 and through the secondary post-infusion line 20 when priming of the apparatus before patient P treatment is performed.

Figure 11:
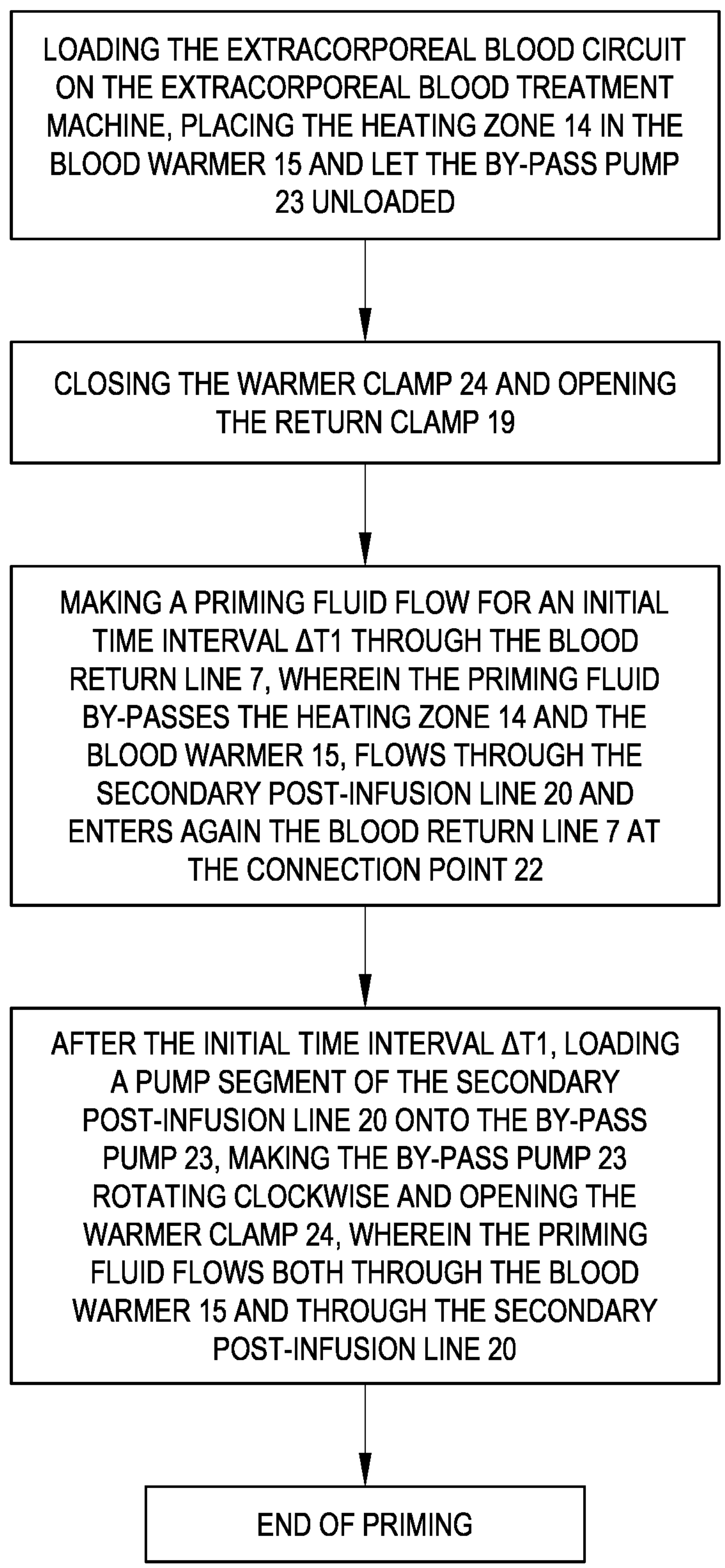
FIG. 11 is a flow chart of a priming procedure of the apparatus of FIG. 3 according to a method of the invention.

To this aim, the extracorporeal blood circuit of the extracorporeal blood treatment apparatus 1 is loaded and filled with the priming fluid so that the priming fluid flows at least through the blood withdrawal line 6, through the blood treatment device 2 and through the blood return line 7 towards the heating zone 14 of said blood return line 7. FIG. 11 shows a flow chart of one example of the priming procedure.

Figure 3:
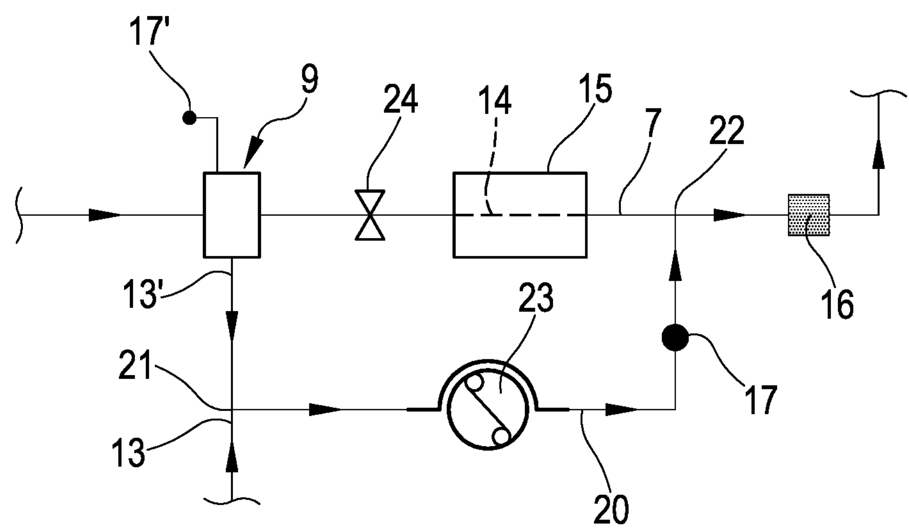
FIG. 3 shows a portion of the apparatus of FIG. 1 in a first operative configuration.

FIG. 3 shows the configuration of the apparatus 1 of FIG. 2 during an initial time interval ΔT1 of the priming procedure. The initial time interval ΔT1 may last for about the time required to flow a priming fluid volume matching with the total blood circuit volume. Priming may be done using the prescribed solutions for the patient treatment.

During said initial time interval ΔT1 the warmer clamp 24 is closed, the return clamp 19 is open. The by-pass pump 23 rotates clockwise to pump fluid from the branching off point 21 towards the connection point 22 or the by-pass pump 23 is not present and not active on the secondary post-infusion line 20 (a pump segment of the secondary post-infusion line 20 is unloaded).

The priming fluid coming from the blood treatment device 2 and flowing through the section of the blood return line 7 placed upstream of the warmer clamp 24 enters the air trapping device 9 but is prevented from entering the heating zone 14.

Therefore, the priming fluid coming from the blood treatment device 2, once in the air trapping device 9, is compelled to flow into the line segment 13' of the post-infusion line 13 (comprised between the air trapping device 9 and the branching off point 21) and then into the secondary post-infusion line 20. Also the priming fluid coming from a source of priming fluid and flowing in a section of the post-infusion line 13 upstream of the branching off point 21 flows into the secondary post-infusion line 20. All the priming fluid by-passes the heating zone 14 and the blood warmer 15 and enters again the blood return line 7 at the connection point 22.

Downstream of the connection point 22, the priming fluid flows towards the terminal end of the blood return line 7.

Figure 4:
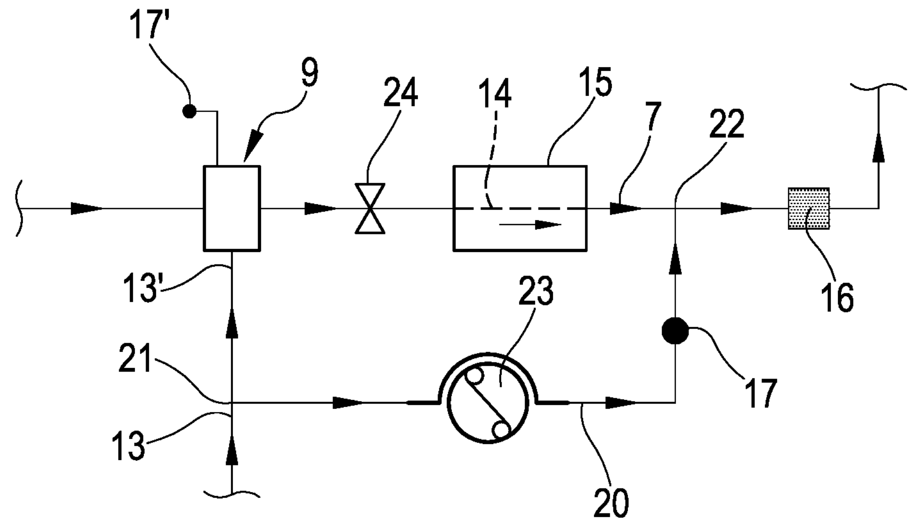
FIG. 4 shows the portion of FIG. 3 in a second operative configuration.

FIG. 4 shows the configuration of the apparatus 1 after the initial time interval ΔT1, during the remaining priming step. During said remaining priming step, the warmer clamp 24 is open, the return clamp 19 is open, the pump segment of the secondary post-infusion line 20 is loaded onto the by-pass pump 23 and the by-pass pump 23 rotates clockwise to pump fluid from the branching off point 21 towards the connection point 22. The by-pass pump 23 is compatible with the priming by-pass phase with relatively high flow rates and air-water mixture. Such a by-pass pump 23 may be a peristaltic pump which pump segment is loaded after the by-pass phase (initial time interval ΔT1). A diaphragm pump or a finger pump may also be considered.

The priming fluid coming from the blood treatment device 2 and flowing through the section of the blood return line 7 placed upstream of the warmer clamp 24 enters and exits the air trapping device 9, flows through a section of the blood return line 7 comprised between the air trapping device 9 and the heating zone 14, then through said heating zone 14 towards the connection point 22. The priming fluid coming from the source of priming fluid and flowing in a section of the post-infusion line 13 upstream of the branching off point 21 is split into the line segment 13' (and then into the air trapping device 9) and into the secondary post-infusion line 20. Indeed, said priming fluid flows in part into the air trapping device 9 and then through the heating zone 14 and in part through the secondary post-infusion line 20 towards the connection point 22. Downstream of the connection point 22, all the priming fluid flows towards the terminal end of the blood return line 7.

Figure 5:
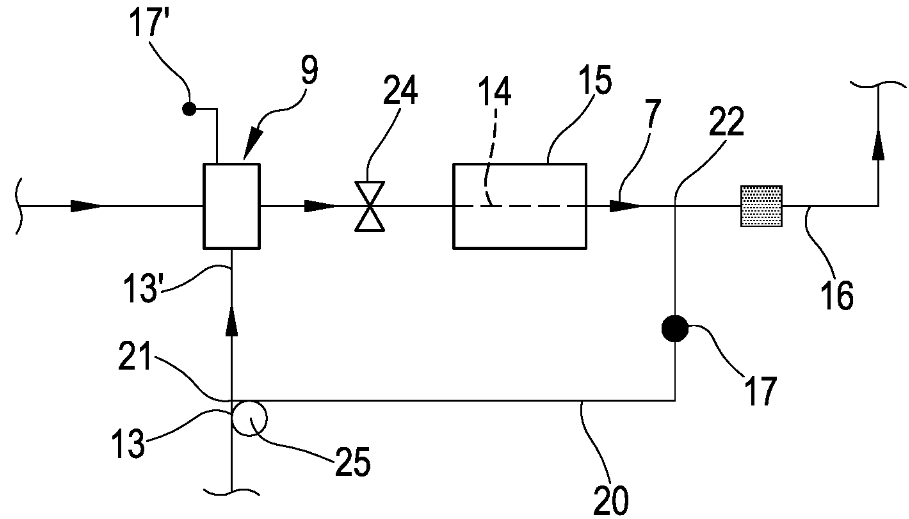
FIG. 5 shows a variant of the portion of FIG. 3 and FIG. 4.

FIG. 5 shows a variant of the apparatus of FIG. 2, in which the by-pass pump 23 is not present and a 3-way pinch valve 25 is placed between the post-infusion line 13 and the secondary post-infusion line 20 at the branching off point 21. Said pinch valve 25 is a control device operatively active on the post-infusion line 13 and on the secondary post-infusion line 20, for controlling a flow through the line segment 13' of said post-infusion line 13 and through said secondary post-infusion line 20.

In use, during patient P treatment the warmer clamp 24 is open. The pinch valve 25 is periodically switched between a first and a second position. In the first position, the pinch valve 25 closes the secondary post-infusion line 20 and let the infusion fluid to flow into the line segment 13' and into the air trapping device 9. In the second position, the pinch valve 25 closes the post-infusion line 13 and let the infusion fluid to flow through the secondary post-infusion line 20 and into the blood return line 7 downstream of the blood warmer 15. The pinch valve design shall be such that, when switching during patient P treatment, no direct communication is present between the air trapping device 9 and the blood return line 7 as to prevent blood flow by-pass through the secondary post-infusion line 20.

When priming, during (warmer clamp 24 closed) and after (warmer clamp 24 open) the initial time interval ΔT1, the pinch valve 25 is set in a neutral position so that the air trapping device 9 is in fluid communication with the secondary post-infusion line 20.

Figure 6:
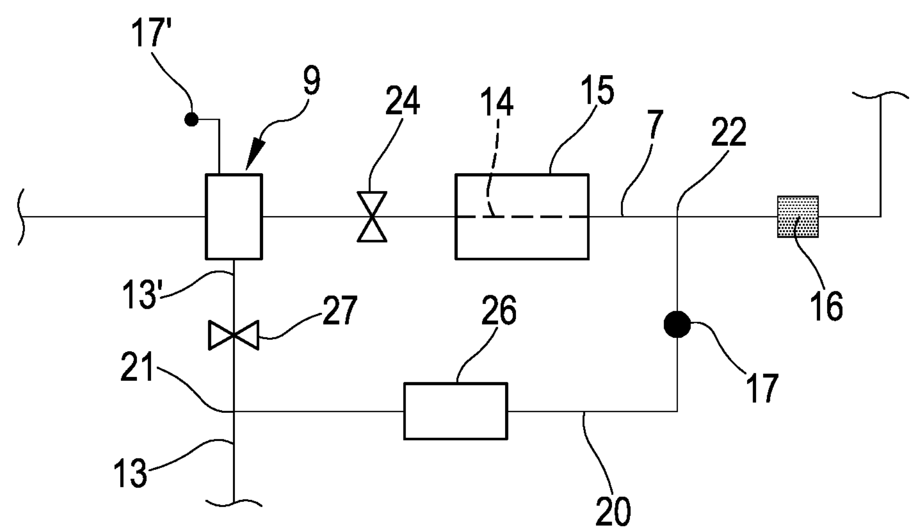
FIG. 6 shows another variant of the portion of FIG. 3 and FIG. 4.

The variant of FIG. 6 differs from the apparatus of FIG. 5 in that the pinch valve 25 is substituted by a flow resistor 26 placed on the secondary post-infusion line 20 in combination with a post-infusion clamp 27 placed on the line segment 13' of the post-infusion line 13 downstream of the branching off point 21. During treatment, this prevents blood flow in the secondary post-infusion line 20 when post-infusion is stopped. The flow resistor 26 may be designed in order to prevent blood flow by-pass in the secondary post-infusion line 20 as soon the post-infusion flow rate is large enough. The post-infusion clamp 27 on the line segment 13' of the post-infusion line 13 is required for preventing blood flow by-pass when post-infusion is stopped.

Figure 7:
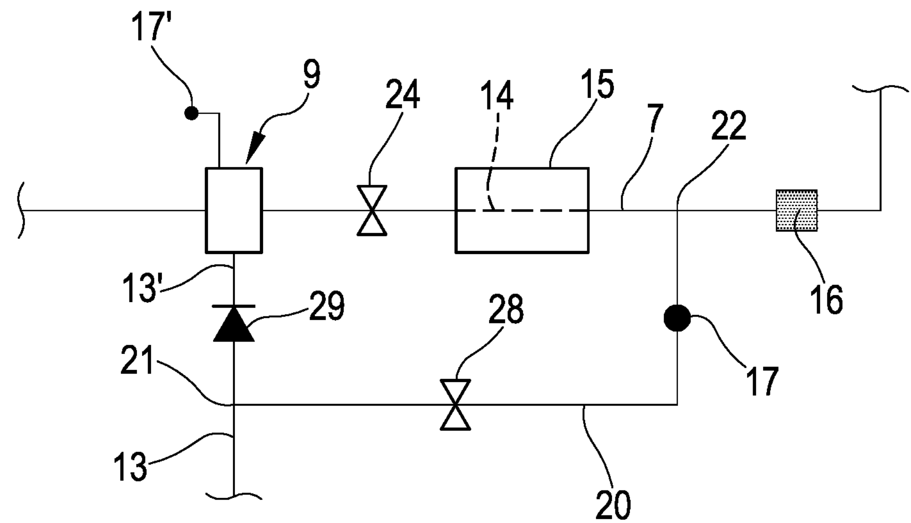
FIG. 7 shows another variant of the portion of FIG. 3 and FIG. 4.

The variant of FIG. 7 differs from the apparatus of FIG. 5 in that the pinch valve 25 is substituted by a secondary post-infusion clamp 28 placed on the secondary post-infusion line 20 in combination with a non-return valve 29 placed on the line segment 13' of the post-infusion line 13 downstream of the branching off point 21

Figure 8:
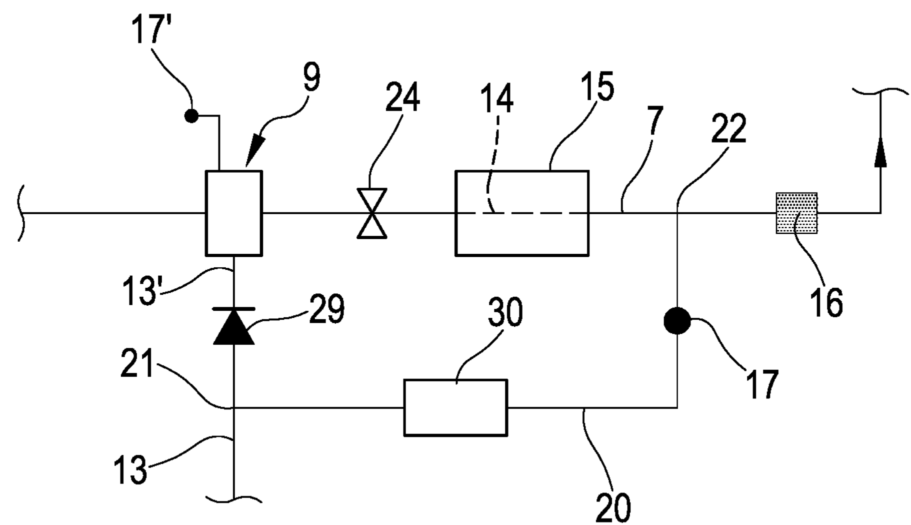
FIG. 8 shows another variant of the portion of FIG. 3 and FIG. 4.

The variant of FIG. 8 differs from the variant of FIG. 7 in that the secondary post-infusion clamp 28 is substituted by a secondary flow resistor 30.

Figure 9:
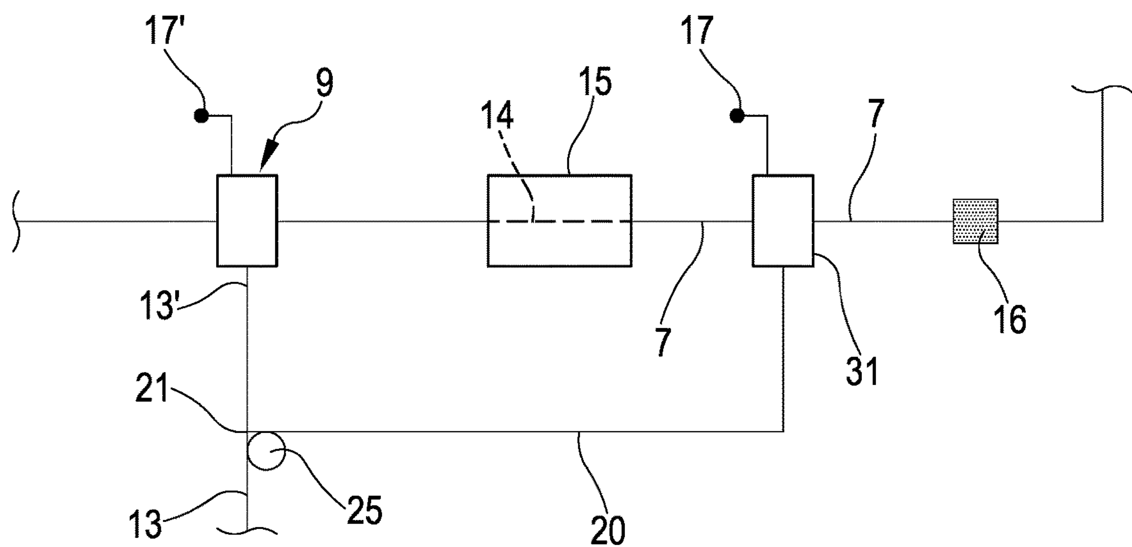
FIG. 9 shows another variant of the portion of FIG. 3 and FIG. 4.

The embodiment of FIG. 9 differs from the apparatus of FIG. 5 in that FIG. 9 further comprises another auxiliary air trapping device 31 and in that no warmer clamp 24 is present. Said auxiliary air trapping device 31 is placed on the blood return line 7 downstream of the heating zone 14 and of the blood warmer 15. Downstream of the heating zone 14, the secondary post-infusion line 20 is connected to the blood return line 7 at the auxiliary air trapping device 31.

Moreover, the return pressure sensor 17 is not on the secondary post-infusion clamp 28 but it is operatively active in the auxiliary air trapping device 31. Optionally, fluid level is automatically monitored in the chambers of both the air trapping devices 9, 31.

Other variants, not shown, of the embodiment of FIG. 9 (in which air trapping devices 9, 31 are present both upstream and downstream of the blood warmer 15) may comprise the control devices (operatively active on the post-infusion lines) shown in FIGS. 2-4 (post-infusion pump 23), 6 (post-infusion clamp 27 and flow resistor 26), 7 (non-return valve 29 and secondary post-infusion clamp 28), 8 (non-return valve 29 and secondary flow resistor 30).

In other variants, not shown, of the embodiment of FIG. 9 (in which air trapping devices 9, 31 are present both upstream and downstream of the blood warmer 15) no post infusion in the auxiliary air trapping device 31 is present. In the case, like in the embodiment of FIG. 1, the blood warmer 15 has not to compensate for any post-infusion cooling effect.

Furthermore, the air trapping device 9 and the auxiliary air trapping device 31 may be each other identical, as in FIG. 9, or the auxiliary air trapping device 31' may be a filled air trap including a soft diaphragm for return pressure measurement.

Figure 10:
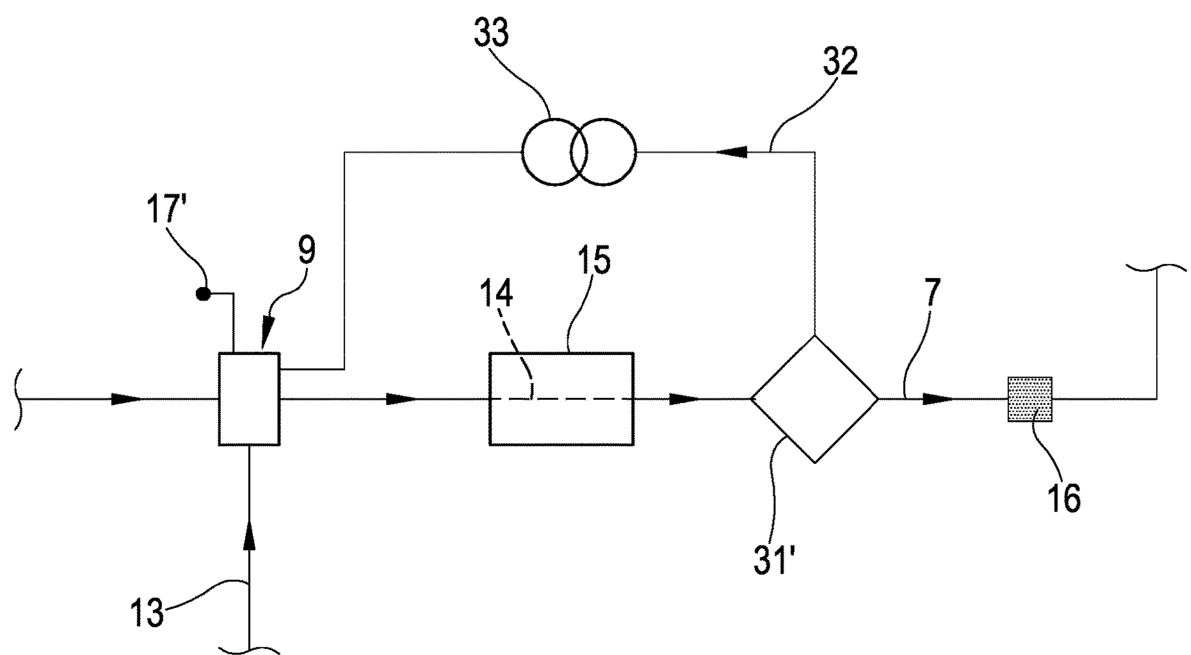
FIG. 10 shows another embodiment of the portion of FIG. 3 and FIG. 4.

FIG. 10 shows the filled air trap 31' and an auxiliary blood line 32 with an auxiliary blood pump 33 connecting the top of the filled air trap 31' to the air trapping device 9.

The auxiliary blood pump 33 may be a peristaltic pump. Pump flow rate might be settled in a wide range from a few ml/min to 100 ml/min and more. This auxiliary blood pump 33 does not need to be stopped in case of alarm and system safe state with stop of the blood pump 8 and return clamp 19 closure. The main purpose of this blood circuit loop is to flow air bubbles back to the air trapping device 9, which should provide for means to remove this air.

In a variant of FIG. 10, not shown, the auxiliary blood pump 33 on the auxiliary blood line 32 is substituted by an additional clamp. This variant plays with the position of two air trapping chamber for making possible the transfer of air bubbles from the filled air trap 31' to the air trapping device 9, when stopping the blood flow and opening the additional clamp.

In another variant of FIG. 10, not shown, the auxiliary blood line 32 is not present.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and the scope of the appended claims.

The invention claimed is:

1. A method for priming an extracorporeal blood circuit of an extracorporeal blood treatment apparatus, before starting patient treatment, the extracorporeal blood treatment apparatus including: (a) a blood treatment device; and (b) a blood warmer, and the extracorporeal blood circuit including: (i) a blood withdrawal line and a blood return line coupled to the blood treatment device, wherein the blood return line includes a heating zone coupled to the blood warmer; (ii) a blood pump configured to be coupled to a pump section either of the blood withdrawal line or of the blood return line; (iii) at least a post-infusion line connected to the blood return line upstream of the heating zone; and (iv) an air trapping device located along the blood return line upstream of the heating zone, the method comprising:

filling the extracorporeal blood circuit of the extracorporeal blood treatment apparatus with a priming fluid, wherein the priming fluid flows at least through the extracorporeal blood treatment device and through at least the blood return line towards the heating zone of said blood return line;

diverting, during an initial time interval, the priming fluid into a secondary post-infusion line to bypass a blood warmer operatively active on said heating zone, wherein the secondary post-infusion line is in fluid communication with the blood return line upstream of the heating zone and is in fluid communication with the blood return line downstream of the heating zone; and directing, after said initial time interval, the priming fluid to flow through an air trapping device placed on the blood return line upstream of the heating zone and then through said heating zone towards a terminal end of the blood return line.

2. The method of claim 1, wherein the extracorporeal blood treatment apparatus includes the secondary post-infusion line in fluid communication with the blood return line upstream of the heating zone and in fluid communication with said blood return line downstream of the heating zone, to bypass the blood warmer.

3. The method of claim 1, wherein during the initial time interval, the priming fluid flows through the post-infusion line connected to the blood return line upstream of the heating zone.

4. The method of claim 1, wherein after the initial time interval, the priming fluid flows through the post-infusion line in fluid communication with the blood return line upstream of the heating zone.

5. The method of claim 1, wherein during the initial time interval, the priming fluid flows through the air trapping device.

6. The method of claim 1, wherein during the initial time interval, the priming fluid flows from the blood return line placed upstream of the heating zone, through the air trapping device and into the secondary post-infusion line.

7. The method of claim 1, wherein after the initial time interval, the priming fluid flows from the post-infusion line in fluid communication with the blood return line upstream of the heating zone, through the air trapping device and into the blood return line downstream of the air trapping device.

8. The method of claim 1, wherein during the initial time interval, a warmer clamp placed on the blood return line between the air trapping device and the heating zone is closed, thus allowing the priming fluid flowing from the post-infusion line, and the priming fluid flowing from the blood return line and through the air trapping device, to flow through the secondary post-infusion line.

9. The method of claim 1, wherein after said initial time interval, the priming fluid, flowing through the post-infusion line in fluid communication with the blood return line upstream of the heating zone, is split into the air trapping device and into the secondary post-infusion line.

10. The method of claim 1, wherein after the initial time interval, the warmer clamp is opened, thus allowing the priming fluid flowing from the post-infusion line to flow through at least one of the secondary post-infusion line and the air trapping device, and allowing the priming fluid flowing from the blood treatment device to flow through the air trapping device and through the heating zone.

11. The method of claim 1, wherein after the initial time interval, the warmer clamp is opened, thus allowing the priming fluid flowing from the post-infusion line to flow through at least one of the secondary post-infusion line and the air trapping device, and allowing the priming fluid flowing from the blood treatment device to flow through the air trapping device and through the heating zone.

12. The method of claim 1, wherein during the initial time interval a post-infusion clamp, placed on the post-infusion line downstream of a branching off point of the secondary post-infusion line, is open so that the air trapping device is in fluid communication with the secondary post-infusion line.

* * * * *